US012736496B1

(12) United States Patent
Koehne et al.

(10) Patent No.: US 12,736,496 B1
(45) Date of Patent: Sep. 15, 2026

(54) ELECTROCHEMICAL SENSORS BASED ON ENZYME-LINKED IMMUNOSORBENT ASSAY

(71) Applicant: United States of America as Represented by the Administrator of NASA, Washington, DC (US)

(72) Inventors: Jessica Erin Koehne, Portola Valley, CA (US); Milton Jorge Santos Cordeiro, San Jose, CA (US); Morgan James Anderson, Sunnyvale, CA (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 446 days.

(21) Appl. No.: 18/163,870

(22) Filed: Feb. 2, 2023

Related U.S. Application Data

(60) Provisional application No. 63/267,481, filed on Feb. 2, 2022.

(51) Int. Cl.

| | |
|---|---|
| ***G01N 27/327*** | (2006.01) |
| ***B03C 1/01*** | (2006.01) |
| ***B03C 1/28*** | (2006.01) |
| ***G01N 33/543*** | (2006.01) |
| ***G01N 33/569*** | (2006.01) |

(52) U.S. Cl.
CPC ........... *G01N 27/3272* (2013.01); *B03C 1/01* (2013.01); *B03C 1/288* (2013.01); *G01N 27/3273* (2013.01); *G01N 27/3276* (2013.01); *G01N 33/5438* (2013.01); *G01N 33/56983* (2013.01); *B03C 2201/18* (2013.01); *B03C 2201/26* (2013.01); *G01N 2469/10* (2013.01)

(58) Field of Classification Search
None
See application file for complete search history.

(56) References Cited

FOREIGN PATENT DOCUMENTS

WO WO-2006008519 A1 * 1/2006 ........... C09D 11/101

OTHER PUBLICATIONS

S.V. Piguillem, et al., “Easily multiplexable immunoplatform to assist heart failure diagnosis through amperometric determination of galectin-3”, Electroanalysis, 32(12): p. 2775-2785, Dec. 2020.*

Anderson, Morgan et al. “Simultaneous, multiplex quantification of protease activities using a gold microelectrode array”, Biosensors and Bioelectronics, vol. 165, 2020, 112330, ISSN 0956-5663, <https://doi.org/10.1016/j.bios.2020.112330>.

(Continued)

*Primary Examiner* — J. Christopher Ball
(74) *Attorney, Agent, or Firm* — Rhys W. Cheung; Trenton J. Roche

(57) ABSTRACT

Electrochemical biological sensors, and more particularly electrochemical biological sensors based on enzyme-linked immunosorbent assay (ELISA) having a microbead detection construct coupled with magnetic immobilization construct. More particularly, Electrochemical ELISA-based biosensors comprising an electrode detection surface; a microbead detection construct; a magnetic immobilization construct; and an electrochemical reporter molecule.

19 Claims, 6 Drawing Sheets

(56) References Cited

OTHER PUBLICATIONS

Song, Yang et al. "Electrochemical Activity Assay for Protease Analysis Using Carbon Nanofiber Nanoelectrode Arrays", Analytical Chemistry 2019, 91(6), 3971-3979, <https://doi.org/10.1021/acs.analchem.8b05189>.

Swisher, Luxi Z. et al. "Quantitative Electrochemical Detection of Cathepsin B Activity in Breast Cancer Cell Lysates Using Carbon Nanofiber Nanoelectrode Arrays toward Identification of Cancer Formation", Nanomedicine, Oct. 2015, 11(7): 1695-1704, <https://doi.org/10.1016/j.nano.2015.04.014>.

* cited by examiner 100
108
104
106
110
112
116
114
102a
102

202
Sensor Surface
201
Sensor

200
Device Wafer

ELECTROCHEMICAL SENSORS BASED ON ENZYME-LINKED IMMUNOSORBENT ASSAY

CROSS-REFERENCE TO RELATED APPLICATIONS

This application claims priority to U.S. Provisional Application 63/267,481 entitled "Viral Antigen Sensor Based on Electrochemical Enzyme-Linked Immunosorbent Assay (ELISA) Microelectrode Array" filed on Feb. 2, 2022.

ORIGIN OF INVENTION

The invention described herein was made in the performance of work under a NASA contract and by (an) employee(s) of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor has elected not to retain title.

BACKGROUND OF THE INVENTION

The present disclosure relates to electrochemical biological sensors, and more particularly to electrochemical biological sensors based on electrochemical enzyme-linked immunosorbent assay (ELISA) sensors consisting of microelectrode arrays (e.g., patterned microelectrode arrays) having a microbead detection construct that enhances binding and signaling coupled with magnetic immobilization construct that provides magnetic sensing enrichment.

Detection of trace biological molecules is important in the healthcare and environmental contexts. For example, in the healthcare context, detection of trace biological molecules, such as proteins, is important to diagnose the early onset of a number of human infections or diseases. For example, diagnosis of the early onset of a coronavirus, such as SARS-COV-2 (viral agent of the COVID-19 disease), allows a diagnosed patient to seek immediate or near immediate treatment, physically quarantine, or take other measures leading to improvement in patient prognoses and reduction of transmission to the general population.

However, concentrations of biological molecules at the early onset of infection or disease are generally so low that traditional detection methodologies do not lend themselves to early detection. Developing sensing technologies with lower limits of detection will lead to earlier diagnosis and improved prognosis. Traditional detection often requires coupling with time-consuming amplification processes, such as polymerase chain reaction (PCR), to increase target analyte concentration to increase concentration to within detectable levels. Conversely, antigen-based tests, such as ELISAs, that use specific antibodies adsorbed to a plate/chip that selectively bind to biological target molecules, such as a SARS-CoV-2 antigen, to produce a signal via reporter enzymes can be effective, but have compromised sensitivity, particularly at the low concentrations of biological molecules indicative of early onset of infection or disease.

Accordingly, there is a need for a biological sensor that provides highly sensitive detection of biological molecules, particularly at low concentrations of said biological molecules for the identification of infection or disease.

SUMMARY OF THE INVENTION

In one or more aspects, the present disclosure provides an electrochemical biosensor based on enzyme-linked immunosorbent assay. The electrochemical biosensor based on enzyme-linked immunosorbent assay includes a microbead detection construct comprising a plurality of signaling molecules and a magnetic immobilization construct.

In one or more aspects, the present disclosure provides a method of detecting a target biological molecule using an electrochemical biosensor based on enzyme-linked immunosorbent assay. The electrochemical biosensor based on enzyme-linked immunosorbent assay includes a microbead detection construct comprising a plurality of signaling molecules and a magnetic immobilization construct. The sensor is exposed to a plurality of reporter molecules and interacted with a magnet.

In one or more aspects, the present disclosure provides a system for detecting a target biological molecule using an electrochemical biosensor based on enzyme-linked immunosorbent assay. The system includes an electrochemical biosensor based on enzyme-linked immunosorbent assay, a frame having a top and a bottom, a plunger having a solenoid and a magnet, wherein the magnet is located above the solenoid and toward the top of the frame, the plunger for vertically moving toward the top and toward bottom of the frame, and a recess in top of the frame for receiving the electrochemical biosensor based on enzyme-linked immunosorbent assay. When the plunger is vertically moved toward the top of the frame, the magnet interacts with the sensor when the sensor is received and positioned within the recess. When the plunger is vertically moved toward the bottom of the frame, the magnet is prevented from interacting with the sensor when the sensor is received and positioned within the recess.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figures 1, 2:
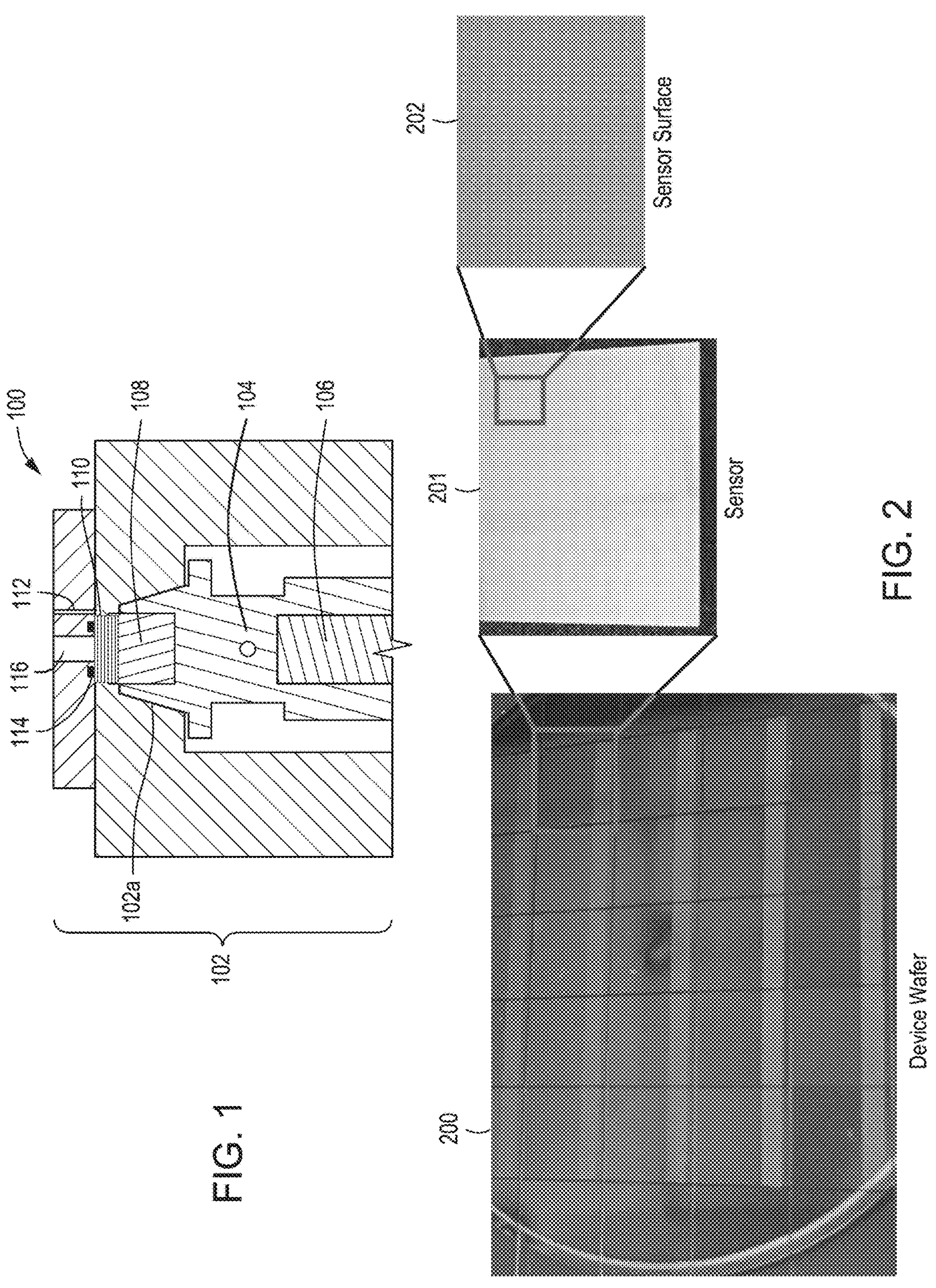
FIG. 1 illustrates a cross-sectional, schematic of an electrochemical cell for testing an electrochemical ELISA-based biosensor, according to one or more aspects of the present disclosure.
FIG. 2 illustrates biosensor chips with a microelectrode array, according to one or more aspects of the present disclosure.

The present disclosure relates to electrochemical biological sensors, and more particularly to electrochemical biological sensors based on electrochemical enzyme-linked immunosorbent assay (ELISA) consisting of microelectrode arrays (e.g., patterned microelectrode arrays) having a microbead detection construct for enhanced binding and signaling coupled with magnetic immobilization construct for magnetic sensing enrichment.

As provided above, traditional methodologies for detection of early onset of infection or disease generally lack sufficient sensitivity to prevent or substantially prevent false negatives and/or false positives, thus potentially preventing accurate information about an ailment. The present disclosure provides electrochemical ELISA-based biosensor apparatuses and methodologies that overcome traditional ELISA-based detection of biological molecules, and further provides other advantages, as described hereinbelow.

The electrochemical ELISA-based biosensors of the present disclosure include an electrode (e.g., single patterned or unpatterned electrode) or microelectrode array (e.g., patterned microelectrode array), a microbead detection construct, a magnetic immobilization construct, and an electrochemical signaling molecule to provide improved sensitivity detection of low concentrations of biological molecules, down to the ~pg/mL range (e.g., the detection of viral antigens, such as that representative of the early onset of infection or disease, including SARS-COV-2). It is to be appreciated that while the present disclosure discusses the electrochemical ELISA-based biosensors with reference to microelectrode arrays, the technology disclosed herein is capable of use with macroelectrodes (e.g., single patterned or unpatterned electrode), without departing from the scope of the present disclosure. Detection of biological molecule(s) of interest may be performed using a liquid or flow cell to house a magnet for connection with an electrochemical reader, as described hereinbelow.

In one or more aspects, unlike traditional ELISA plate and optical reader platforms, the electrochemical ELISA-based biosensors of the present disclosure advantageously incorporate the microbead detection construct coupled with the magnetic immobilization construct, which substantially increases the signal sensitivity of the sensor. The microbead detection construct is characterized by high loading of a signal-generating enzyme. The magnetic immobilization construct draws the microbead detection construct to an electrode detection surface or microelectrode array detection surface upon antigen binding, the microelectrode array comprising conductive microdots (i.e., working electrode microdots), wherein the microbead detection construct and surface enhance signal sensitivity (e.g., due to regenerative redox reaction).

Indeed, the electrochemical ELISA-based biosensors of the present disclosure advantageously demonstrate an elevated signaling strength compared to traditional ELISA in appreciable magnitudes. For example, traditional ELISA plate-based testing exhibits five (5) to ten (10) signaling molecules per probe molecule (e.g., antibody) binding event, whereas the electrochemical ELISA-based biosensors of the present disclosure exhibit up to 4,857 signaling molecules per probe molecule (e.g., antibody) events. Without wishing to be bound by theory, the increase in signal sensitivity is due to the large number, and is increased in comparison to traditional optical ELISA approaches, of signaling molecules on the microbead detection construct. Moreover, the model bead construct of the present disclosure exhibits an increase in measured signal of equal to or over 6.75-fold and an equal to or greater 35.7-fold improvement in signal sensitivity compared to traditional ELISA approaches. The increase in signal and improvement in signal sensitivity using the electrochemical ELISA-based biosensors of the present disclosure are reported based on the model bead construct described hereinbelow. Without wishing to be bound by theory, the increase in signal and improvement in signal sensitivity is due to increased localization of electrochemical redox signaling molecules coupled with redox cycling onto the macroelectrode or microelectrode array detection surface, compared to traditional ELISA approaches.

Moreover, depending on the particular electrochemical reporter molecule (e.g., tetramethyl benzidine (TMB)), the electrochemical ELISA-based biosensors of the present disclosure may be used for optical sensing and/or colorimetric sensing, alone or in addition to electrochemical sensing. Optical sensing combined with electrochemical sensing may increase the dynamic sensing range of the electrochemical ELISA-based biosensors described herein.

The electrochemical ELISA-based biosensors of the present disclosure are advantageously adaptable for detecting a variety of biological molecules, including simultaneously detecting two or more biological molecules. Indeed, in combination with chemical modification(s) of the magnetic immobilization construct and the microbead detection construct, the Electrochemical ELISA-based biosensors of the present disclosure are advantageously capable of detecting multiple biological molecules to diagnose not only human (or animal) disease, but also for detection of environmental contaminants (e.g., during environmental monitoring). When compared to the optical ELISA, the electrochemical ELISA sensor of the present disclosure improves the limit of detection up to a factor of 60.5.

Moreover, the electrochemical ELISA-based biosensors of the present disclosure may be adapted to provide the option for point-of-care testing or in-home-testing, thus allowing patient or caregiver use without having to seek a professional healthcare provider or testing center.

Definitions

As used herein, the term "frame," and grammatical variants thereof, refers to a structure or chassis which is used to hold the microelectrode array (e.g., patterned microelectrode arrays) or macroelectrode chip inside an electrochemical cell and to introduce a magnetic field to the electrochemical cell. Configurations of the frame of the present disclosure include, but are not limited to, a 3D printed structure which holds a solenoid with an attachment on a solenoid plunger to hold the a permanent magnet below a baseplate holding the microelectrode array or macroelectrode chip and a top portion to seal the sensor.

As used herein, the term "electrochemical cell," and grammatical variants thereof, refers to the position where measurements are made. Configurations of the frame of the present disclosure include, but are not limited to, a cavity of the frame above the microelectrode array or macroelectrode chip where a counter electrode and reference electrode are placed. The cavity is filled with appropriate analyte solution to contact all of the electrodes.

As used herein, the terms "electrochemical ELISA-based biosensor," "ELISA sensor" or simply "sensor," as grammatical variants thereof, refer to the sensors of the present disclosure comprising at least an electrode or microelectrode array detection surface, a microbead detection construct, a magnetic immobilization construct, and an electrochemical reporter molecule, unless otherwise explicitly stated. Configurations of the electrochemical ELISA-based biosensors of the present disclosure are described hereinbelow and include a magnetic surface located beneath the electrode or microelectrode detection surface.

As used herein, the term "biological molecule," and grammatical variants thereof, refers to any detectable target molecule produced by or detectable within a biological entity, including biological entities themselves, such as entities detectable by antibody detection, single-stranded DNA (optionally functionalized) detection, aptamer detection, and the like, and any combination thereof, without limitation. Such biological molecules may include, but are not limited to, proteins (e.g., viruses, bacterium), peptides (e.g., viruses, bacterium), small molecules (e.g., cortisol, narcotics), nucleic acids, pharmaceuticals (e.g., anti-drug antibodies), enzymes (e.g., proteases for muscle atrophy), and any combination thereof, depending on the design of a particular electrochemical ELISA-based bio sensor configuration according to one or more aspects of the present disclosure. Accordingly, the biological molecule may be present within an animal (e.g., mammals, reptiles, birds, amphibians, fish, invertebrates) or within another medium in which a biological molecule may exist (e.g., water, sewage, soil, snow). Thus, the electrochemical ELISA-based biosensors of the present disclosure may be utilized for a variety of end-uses, including healthcare monitoring, infection or disease detection, environmental monitoring, and the like, and any combination thereof. Herein, the term "biological molecule" may refer to antigens.

The biological molecules may be present in a biological fluid and/or environmental fluid including, but is not limited to, serum, blood, urine, perspiration, tears, saliva, nasal mucus, water supplies (e.g., lakes, oceans, rivers), sewage, soils, and the like, and any combination thereof.

As used herein, the term "substrate," and grammatical variants thereof, refers to an initial material used to fabricate the microelectrode array or macroelectrode chips. In the present disclosure the substrate includes, but is not limited to, a 100 mm silicon wafer with approximately 1.0 μm of thermally oxidized silicon dioxide (SiO2).

As used herein, the term "electrode" or "electrode detection surface," and grammatical variants thereof, refers to a single electrode surface. As used herein, the term "microelectrode array" or "microarray detection surface," and grammatical variants thereof, refers to a plurality of spaced-apart, conductive microdots (i.e., working electrodes) on a single substrate. The microelectrode array detection surface may be prepared using traditional, lithographic cleanroom microfabrication techniques, although other known fabrication techniques are also within the scope of the present disclosure, without limit. As provided above, a macroelectrode (or macroelectrode detection surface) may additionally be used in the methodologies described herein, having an unpatterned conductive surface, without departing from the present disclosure and thus are equally applicable when the term "microelectrode array" is used. Unless otherwise stated, the terms "electrode" or "electrode detection surface" will be used interchangeably hereinbelow to refer to a single electrode detection surface, a microelectrode array detection surface, or a macroelectrode detection surface.

As used herein, the term "microdot," and grammatical variants thereof, refers to a conductive material applied upon a biosensor chip substrate (e.g., a wafer-size silicon chip, or other substrate).

In one or more aspects of the present disclosure, the electrode detection surface of the present disclosure may include a patterned gold microelectrode array or an unpatterned macroelectrode, each fabricated upon a silicon wafer chip substrate.

As used herein, the term "interspatial distance," and grammatical variants thereof, refers to the distance between adjacent microdots within a microelectrode array or macroelectrode and upon a biosensor chip substrate, representing the spaced-apart nature of the microdots radially in all directions. The interspatial distance may also be referred to as "pitch."

As used herein, the term "magnetic immobilization construct," or simply "immobilization construct," and grammatical variants thereof, refers to an electrochemical ELISA-based sensor element comprising a magnetic microbead functionalized with one or more immobilization molecules. The magnetic microbeads may be, but need not be, coated with a polymer.

In one or more aspects of the present disclosure, the magnetic immobilization construct of the present disclosure may include a streptavidin magnetic microbead functionalized with N-Protein immobilization antibody molecules via biotin-streptavidin chemistry.

As used herein, the term "immobilization antibody molecules" or simply "immobilization antibody," and grammatical variants thereof, refers to molecules (i.e., nucleic acids, antibodies, aptamers, proteins, peptides, nanobodies, etc.) adsorbed onto the magnetic immobilization construct that allow for the specific binding to a target analyte.

As used herein, the term "detection antibody molecules" or simply "detection microbead" or "detection antibody," and grammatical variants thereof, refers to molecules (i.e., nucleic acids, antibodies, aptamers, proteins, peptides, nanobodies, etc.) adsorbed onto the detection microbead construct that allow for the specific binding to a target analyte.

As used herein, the term "microbead detection construct," or simply "detection construct," and grammatical variants thereof, refers to an electrochemical ELISA-based sensor element comprising detection microbeads functionalized with one or more signaling molecules (e.g., enzymes) and detection molecules (e.g., antibodies) for electrochemical signaling. It is to be noted that the term "detection microbead" is used merely to distinguish between the magnetic microbead used as part of the magnetic immobilization construct. The detection microbead does not itself provide the positive response signal.

The terms "signaling molecule" and "enzyme," and grammatical variants thereof, with respect to the microbead detection construct, are used interchangeably herein (i.e., horseradish peroxidase (HRP), alkaline phosphatase, etc.).

In one or more aspects of the present disclosure, the microbead detection construct of the present disclosure may include a polystyrene detection microbead co-functionalized with a signaling molecule and N-Protein detection antibody molecules.

As used herein, the term "reporter molecule," and grammatical variants thereof, refers to a compound added to a sample comprising a biological molecule of interest, which may be in a buffer solution, that interacts with the signaling molecule(s) of the detection construct that, due to close proximity to the electrode detection surface, is able to be regenerated and amplify response signal.

In one or more aspects of the present disclosure, the reporter molecule may be 3,3',5,5'-tetramethylbenzidine (TMB); 2,2'-azino-bis(3-ethylbenzthiazoline-6-sulfonic acid); 4,4'-diaminobiphenyl; 3,3'-diaminobenzidine; o-phenylenediamine; 2-methoxyphenol; Hydroxybenzene; 1-amino-4-methylbenzene; 3,3'-dimethylbenzidine; 1,4-dihydroxybenzene; 4-amino-2,3-dimethyl-1-phenyl-3-pyrazolinone; 5-aminosalicylic acid; 4-chloro-1-naphthol; and the like; and any combination thereof.

As used herein, the term "reaction cascade," and grammatical variants thereof, refers to an electrochemical redox reaction in which electrons are transferred between reactants of the electrochemical ELISA-based biosensors of the present disclosure and the electrode surface, as described hereinbelow, for reporter molecule detection.

With reference to the Examples provided hereinbelow, the term "model bead construct" or simply "model construct," and grammatical variants thereof, refers to a magnetic microbead functionalized with horseradish peroxidase (HRP) via biotin-streptavidin chemistry; and the term "full bead construct" or simply "full construct," and grammatical variants thereof, refers to an immobilization construct and a detection construct linked via binding to a target antigen, e.g., that of SARS-COV-2 nucleocapsid protein (N-Protein).

One or more (two or more, etc.) magnets are used in combination with the electrochemical ELISA-based biosensors of the present disclosure to interact with the magnetic immobilization construct described herein. As used herein, the term "magnet," and grammatical variants thereof, refers to any material producing a magnetic field and of appropriate size and strength to immobilize the magnetic immobilization construct. Suitable magnets may include, but are not limited to, neodyminum, iron, nickel, cobalt, ferritic stainless steel, iron oxide, and the like, the selection of which may depend upon the particular magnetic immobilization construct. Various magnets are used in the present disclosure for various tasks (i.e. purification of immobilization constructs during functionalization, for washing the immobilization complex during the detection assay and enrichment during electrochemical measurement). The function of the selected magnet should be clear from the particular task. Moreover, the magnet(s) may be an electromagnet.

Electrochemical ELISA-Based Biosensors and Methodologies Based on Enzyme-Linked Immunosorbent Assay While one or more aspects of the electrochemical ELISA-based biosensors and methods related thereto of the present disclosure may be made with reference to viral antigen detection, such as detection of SARS-COV-2, it is to be appreciated that the electrochemical ELISA-based biosensors described herein may be adapted for detection of any of one or more of the biological molecules defined herein, without departing from the scope of the present disclosure.

The present disclosure provides electrochemical ELISA-based biosensors that include at least an electrode detection surface, a microbead detection construct, a magnetic immobilization construct, and an electrochemical reporter molecule to provide improved signal sensitivity for the detection of biological molecules, particularly at low concentrations.

The various aspects of the electrochemical ELISA-based biosensors of the present disclosure will primarily be described with reference to the Examples hereinbelow, including electrochemical ELISA-based biosensor apparatus configurations (e.g., hardware structures) and methodologies related thereto.

The electrochemical ELISA-based biosensor apparatus configurations provide magnetic enrichment, electrochemical redox cycling of the reporter molecule(s), and reduction of capacitive charging, among other advantages.

For example, the electrochemical ELISA-based biosensors of the present disclosure are magnetically enriched, wherein the sensors are designed such that the microbead detection construct (and signaling molecules associated therewith) is brought within close proximity to the electrode detection surface to enhance biological molecule detection. As such, the signaling molecules (e.g., HRP) are concentrated near the electrode detection surface.

The electrochemical ELISA-based biosensors of the present disclosure maximize electrochemical redox cycling. By reducing the distance between the signaling molecules of the microbead detection construct and the electrode detection surface, regeneration of a reporter molecule(s) can be achieved, as described herein with reference to FIG. 9B. This regeneration of the reporter molecule prevents depletion thereof at the surface of the microbead detection construct over time and results in a positive electrochemical feedback loop. It is to be noted, however, that even without a positive electrochemical feedback loop, the electrochemical ELISA-based biosensors of the present disclosure are believed to exhibit enhanced electrochemical signal and signal sensitivity due to their configuration (e.g., close proximity of the signaling molecules to the electrode detection surface).

In one or more additional aspects, the electrochemical ELISA-based biosensors described herein utilize microelectrode array detection surfaces, which reduce capacitive charging (i.e., electrochemical interference) and is believed to additionally contribute to the enhancements of the electrochemical ELISA-based biosensor.

The electrochemical ELISA-based biosensor methodologies of the present disclosure provide configurations for the microbead immobilization construct, the microbead detection construct, and for the interaction between the two constructs to capture a biological molecule (antigen) of interest, among other advantages. For example, the microbead detection construct of the present disclosure may consist of a polystyrene microbead conjugated to additional polystyrene microbeads, all of which are decorated with signaling molecules (e.g., HRP), thereby yielding increased signaling molecule per target biological molecule capture (or "conjugation") and amplifying signal. Moreover, the electrochemical ELISA-based biosensor described herein includes fluid handling methodologies for biological molecule detection.

In one or more aspects, the electrode detection surface (i.e., the working electrode(s)) of the present disclosure may be a single surface, macroelectrode, or provided as a microelectrode array. The electrode detection surface is comprised of a conductive material including, but not limited to, gold, carbon (e.g., carbon nanotubes), platinum, copper, silver, aluminum, titanium, indium tin oxide, boron doped diamond and the like, and any combination thereof. In certain aspects of the present disclosure, the electrode detection surface is gold. The electrode detection surface (microelectrode arrays and/or macroelectrodes) may be of any shape, without limitation, including circular, ovoid, square, rectangular, polygonal, or asymmetric, without limitation. When the electrode detection surface comprises a microelectrode array of spaced-apart microdots, the microdots have an average diameter in the range of about 1 μm to about 10 μm. In some embodiments, the sensor chip comprised of the electrode detection surface encompasses a length or width of any value or subset between 100 μm and 450 mm. In some embodiments, the substrate may comprise, for example, but not be limited to, silicon, glass, quartz, a polymer (e.g., polyethylene terephthalate, KAPTON®), and the like, and any combination thereof, encompassing a length or width any value or subset there between 25 mm to 450 mm. In some embodiments, the sensor chip is small than or up to the size of the substrate.

In certain aspects of the present disclosure, the sensor chip is 14 mm by 14 mm and the substrate is 100 mm diameter.

As provided above, the microdots are spaced-apart, having a minimum interspatial distance between each microdot of greater than about 10 μm, such as in the range of about 10 μm to about 50 μm, encompassing any value and subset therebetween, such as about 10 μm to about 40 μm, or about 20 μm to about 40 μm.

Counter and reference electrodes or combination counter/reference electrodes, typically platinum and/or silver/silver chloride, may be fabricated in proximity with the electrode detection surface, separated by a dielectric, such as on the same biosensor chip substrate as a microelectrode array, or added to a measurement liquid cell.

The magnetic microbeads for use in the magnetic immobilization construct may be composed of any magnetic material suitable for direct or indirect (e.g., atop the electrode detection surface disposed upon the magnet) adherence to the magnet described herein based on polarity, including, but not limited to, any of the magnet materials described hereinabove and materials exhibiting other forces may additionally be present such as electrostatic, van der Waals forces, and the like, and any combination thereof. The magnetic microbeads may be composed of iron oxide, for example. In one or more aspects, the magnetic microbeads may be coated with one or more polymers and/or proteins for functionalization with an immobilization molecule (e.g., antibody). For example, the magnetic microbeads may be coated with streptavidin protein to facilitate biotin-streptavidin chemistry binding.

The detection microbeads for use in the microbead detection construct may be composed of any material that does not interfere with the magnet or other components of the electrochemical ELISA-based biosensor described herein. Examples of suitable materials for the detection microbeads may include, but are not limited to, polystyrene, polycarbonate, ceramic, polypropylene, polyvinyl carbonate, silica, epoxy, and the like, and any combination thereof. In some instances, the detection microbeads are composed of polystyrene and functionalized with a signaling molecule and a detection molecule (e.g., antibody) for binding to a target biological molecule.

The magnetic microbeads and detection microbeads may be of the same or different size, without limitation. Generally, the magnetic and detection microbeads have an average diameter in the range of about 0.1 μm to about 1.5 μm, encompassing any value and subset therebetween, such as about 0.1 μm to about 0.3 μm, or about 0.3 μm to about 0.6 μm, or about 0.6 μm to about 1.0 μm, or about 1.0 μm to about 1.5 μm.

In one or more aspects of the present disclosure, the signaling molecule may include, but is not limited to, HRP. In some instances, the reporter molecule can be TMB.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention elements and features disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time consuming, such efforts would be, nevertheless, a routine undertaking for those of ordinary skill the art and having benefit of this disclosure.

While compositions and methods are described herein in terms of "comprising" various components or steps, the compositions and methods can also "consist essentially of" or "consist of" the various components and steps.

Embodiments disclosed herein include:

Embodiment A: An electrochemical biosensor based on enzyme-linked immunosorbent assay, comprising: an electrode detection surface; a microbead detection construct comprising a plurality of signaling molecules; and a magnetic immobilization construct.

Embodiment B: A method comprising: providing an electrochemical biosensor based on enzyme-linked immunosorbent assay, the sensor comprising: an electrode detection surface; a microbead detection construct comprising a plurality of signaling molecules; and a magnetic immobilization construct; exposing the sensor to a plurality of reporter molecules; contacting the sensor with a magnet; detecting the presence of one or more biological molecules based on one or both of an electrochemical signal or an optical signal from at least a portion of the plurality of reporter molecules.

Embodiment C: A system comprising: an electrochemical biosensor based on enzyme-linked immunosorbent assay; a frame having a top and a bottom; a plunger comprising a solenoid and a magnet, wherein the magnet is located above the solenoid and toward the top of the frame, the plunger for vertically moving toward the top and toward bottom of the frame; and a recess in top of the frame for receiving an electrochemical biosensor based on enzyme-linked immunosorbent assay, wherein vertically moving the plunger toward the top of the frame causes the magnet to interact with the electrochemical biosensor based on enzyme-linked immunosorbent assay when the electrochemical biosensor based on enzyme-linked immunosorbent assay is received by the recess, and wherein vertically moving the plunger toward the bottom of the frame prevents the magnet from interacting with the electrochemical biosensor based on enzyme-linked immunosorbent assay when the electrochemical biosensor based on enzyme-linked immunosorbent assay is received by the recess.

Each of Embodiments A and B may have one or more of the following Elements in any combination:

Element 1: wherein the electrode detection surface is a microelectrode array detection surface comprising a plurality of microdots.

Element 2: wherein the electrode detection surface is a microelectrode array detection surface comprising a plurality of microdots, and wherein the plurality of microdots have an average diameter in the range of about 1 μm to about 10 μm.

Element 3: wherein the electrode detection surface is a microelectrode array detection surface comprising a plurality of microdots, and wherein the plurality of microdots have an interspatial distance in the range of about 10 μm to about 50 μm.

Element 4: wherein the microbead detection construct comprises a detection microbead co-functionalized with a plurality of SARS-COV-2 N-Protein detection antibody and the plurality of signaling molecules.

Element 5: wherein the microbead detection construct comprises a detection microbead co-functionalized with a plurality of SARS-COV-2 N-Protein detection antibody and the plurality of signaling molecules, and wherein the microbead is composed of a material selected from the group consisting of polystyrene, polycarbonate, ceramic, polypropylene, polyvinyl carbonate, silica, epoxy, and any combination thereof.

Element 6: wherein the microbead detection construct comprises a detection microbead co-functionalized with a plurality of SARS-COV-2 N-Protein detection antibody and the plurality of signaling molecules, and wherein the detection microbead has a diameter in the range of about 0.1 μm to about 1.5 μm.

Element 7: wherein the microbead detection construct comprises a detection microbead co-functionalized with a plurality of SARS-COV-2 N-Protein detection antibody and the plurality of signaling molecules, and wherein the plurality of detection antibodies detect SARS-COV-2 N-Protein.

Element 8: wherein the plurality of signaling molecules are electrochemical signaling molecules.

Element 9: wherein the plurality of signaling molecules are horseradish peroxidase enzymes.

Element 10: wherein the magnetic immobilization construct comprises a magnetic microbead functionalized with a plurality of immobilization antibodies.

Element 11: wherein the magnetic immobilization construct comprises a magnetic microbead functionalized with a plurality of immobilization antibodies, and wherein the magnetic microbead is composed of a ferro-magnetic material selected from the group consisting of but not limited to iron oxide, nickel, cobalt and any combination thereof.

Element 12: wherein the magnetic immobilization construct comprises a magnetic microbead functionalized with a plurality of immobilization antibodies, and wherein the magnetic microbead has a diameter in the range of about 0.1 μm to about 1.5 μm.

Element 13: wherein the magnetic immobilization construct comprises a magnetic microbead functionalized with a plurality of immobilization antibodies, and wherein the plurality of immobilization antibodies detects SARS-CoV-2 N-Protein.

Element 14: wherein the magnetic immobilization construct is contacted with the electrode detection surface by magnetic field interaction with a magnet located beneath the electrode detection surface.

Element 15: wherein the wherein the detection construct and the magnetic immobilization construct are configured to bind a target biological molecule, and wherein the detection construct and the magnetic immobilization construct associate upon both binding the target biological molecule of interest.

Embodiment B may have one or more of the following additional Elements in any combination with Elements 1-15 above:

Element 16: wherein the exposing is before the contacting or the contacting is before the exposing.

Embodiment B may have one or more of the following additional Elements in any combination with Elements 1-15 above:

Element 17: wherein the electrochemical biosensor based on enzyme-linked immunosorbent assay comprises: an electrode detection surface; a microbead detection construct comprising a plurality of signaling molecules; and a magnetic immobilization construct.

To facilitate a better understanding of the embodiments of the present invention, the following examples of preferred or representative embodiments are given. In no way should the following examples be read to limit, or to define, the scope of the invention.

EXAMPLES

The electrochemical ELISA-based biosensors of the present disclosure, as provided above, include at least a microelectrode array, a microbead detection construct, a magnetic immobilization construct, and an electrochemical reporter molecule to provide improved rapid testing of biological molecules.

Testing Equipment

The following Examples were tested using a laboratory electrochemical cell, a cross-sectional, schematic illustration is shown in FIG. 1. Electrochemical cell 100 comprises a 3D printed frame 102 of polylactic acid (PLA). The frame 102 holds a solenoid (solenoid body not shown) with a 3D printed PLA plunger attachment 104 connected to the solenoid plunger 106. The 3D printed PLA plunger attachment 104 has a cavity to seat a permanent magnet 108 of neodymium. As shown, a cavity **102*a* is provided in the frame 102 for receiving the plunger attachment 104. A recess is also provided in the frame 102 for receiving an electrochemical ELISA-based biosensor 110 according to the present disclosure, the electrode detection surface being in contact with the frame 102 recess. The top portion of the frame 102 receiving the ELISA-based sensor 110 of the electrochemical cell 100 is wax-treated to make it waterproof and contains a pogo-pin 112 to make electrical contact with the electrode detection surface of the ELISA-based sensor 110 and an O-ring 114 to prevent fluid leakage. A fluid cavity 116 is included to deploy and apply fluid and other elements (e.g., reporter molecule) onto the electrochemical ELISA-based biosensors. A silver/silver chloride reference electrode (not shown) and a platinum counter electrode (not shown) are further used for electrochemical measurements. Additional electronics (not shown) include a power supply for the solenoid 106 and a microcontroller to receive signals from the potentiostat and to time the raising/lowering of the solenoid plunger 106, solenoid plunger attachment 104 and the permanent magnet 108**.

The electrode detection surface of ELISA-based sensor 110 was configured according to FIGS. 2A and 2B for use in the Examples described herein. FIG. 2 shows a top view of biosensor chips 200, having a microelectrode array 201 of gold microdots (exploded view 202).

Figure 3A:
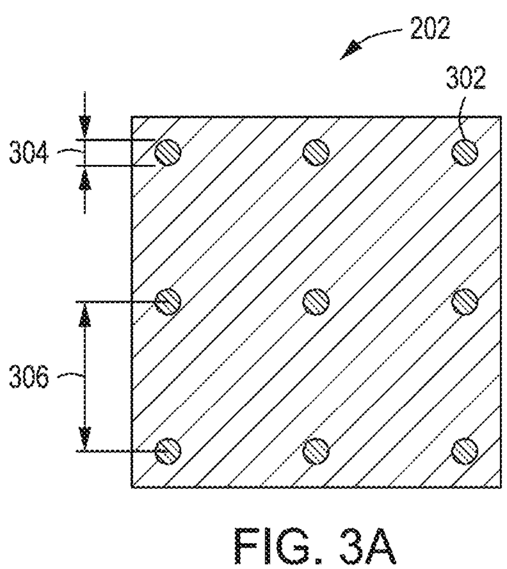
FIG. 3A illustrates a top view, schematic of a microelectrode array of microdots, according to one or more aspects of the present disclosure.
Figure 3B:
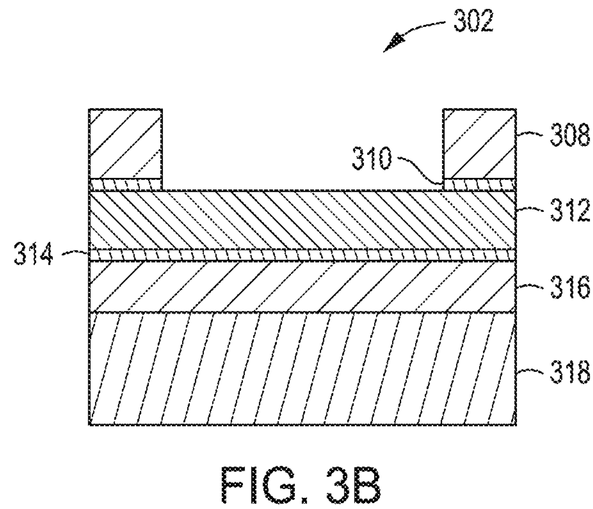
FIG. 3B illustrates a cross-sectional, schematic view of the composition of an electrode detection surface formed upon a biosensor chip, according to one or more aspects of the present disclosure.

Referring now to FIGS. 3A and 3B, illustrated are schematic views of the surface of biosensor chip 201 of FIG. 2 and the composition of each microelectrode array detection surface (microdot) of biosensor chip 202 of FIG. 2. Referring first to FIG. 3A, a top view, schematic of biosensor chip 202 shows microdots 302. Each microdot 302 has a diameter 304 and between each microdot is an interspatial distance (pitch) 306. The Examples provided herein include microdots 302 having diameters 304 in the range of 2 μm to 10 μm, and interspatial distances 306 in the range of 20 μm to 40 μm.

FIG. 3B is a cross-sectional, schematic view of the composition of the electrode detection surface (microdot 302) formed upon a biosensor chip 201 (FIG. 2) having a layered composition of silicon dioxide and/or silicon nitride, titanium, and gold patterned onto a silicon substrate by traditional, lithographic cleanroom microfabrication techniques. As shown, and for use in the Examples provided herein, the layered configuration includes, from top to bottom, first silicon dioxide layer 308 (1 μm), first titanium adhesion layer 310 (20 nanometers (nm)), gold electrode layer 312 (100 nm), second titanium layer 314 (20 nm), second titanium adhesion layer 316 (500 nm), and silicon substrate 318 (Si<100>).

The following Examples were preformed to optimize electrochemical detection and elements of the electrochemical ELISA-based biosensors described herein. Examples were performed using either the model bead construct or the full bead construct, as defined hereinabove and described hereinbelow.

The following terms will be used in the Examples, as defined below, unless specified otherwise:

The term "Buffer" comprises tris-buffered saline (TBS) (1×), 0.01% Tween-20, pH 7.4.

The term "Magnetic Microbead" or simply "Magnetic Bead" is a PIERCE™ Streptavidin Magnetic Bead (10 mg/mL) (ThermoFisher Scientific, Waltham, MA), having an average diameter of 1 μm. The term "immobilization microbead construct" or simply "immobilization bead" is a magnetic bead functionalized with immobilization antibodies, such as those specific to SARS-COV-2 nucleocapsid protein (N-Protein) (GeneTex, Cat No. GTX635685, Irvine, CA).

The term "Detection Microbead" or simply "Detection Bead" is a polystyrene bead (average diameter of 0.276 μm) co-functionalized with horseradish peroxidase (HRP) and detection antibodies, such as those specific to SARS-COV-2 nucleocapsid protein (N-Protein) (GeneTex, Cat No. GTX635712, Irvine, CA).

The term "TMB Solution" is 1-STEP™ Ultra TMB-ELISA Substrate Solution (ThermoFisher Scientific) containing a proprietary mixture of TMB, surfactant, and buffer.

Model Bead Construct Examples

The model bead construct was developed (magnetic beads functionalized with HRP) to screen electrochemical and optical methodologies and different microelectrode array configurations and to broadly assess electrochemical performance and magnetic enhancement. The model bead construct Examples are analogous to traditional ELISA, except with magnetic bead constructs.

The model bead construct was prepared as follows:

(1) Add 50.0 microliters (μL) (0.5 milligrams (mg)) Magnetic Beads into a microcentrifuge tube;
(2) Place the tube into a magnetic stand for 3 minutes (min) to collect the magnetic beads against the side of the tube;
(3) Remove and discard the supernatant;
(4) Add 1.00 mL Buffer to the tube;
(5) Vortex gently and collect the Magnetic Beads with a magnetic stand;
(6) Remove and discard the supernatant;
(7) Suspend the Magnetic Beads in 300.00 μL of Buffer;
(8) Add 10.00 micrograms (μg) of biotinylated HRP;
(9) Incubate for 1 hour and 40 min (700 rpm constant agitation) at room temperature (RT);
(10) Repeat step 2 and 3 ten times; and
(11) Suspend pellet in 1.00 mL of Buffer.

Figure 4:
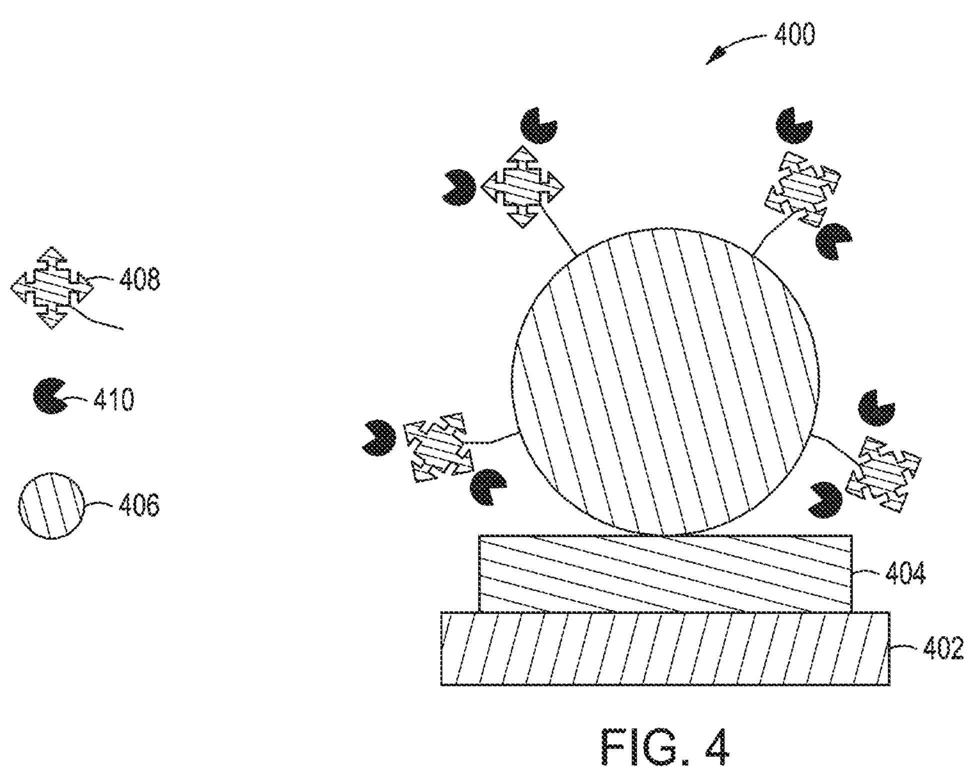
FIG. 4 illustrates a schematic of the model bead construct in association with the magnet of the electrochemical testing cell, according to one or more aspects of the present disclosure.

FIG. 4 illustrates a schematic of the model bead construct 400 in association with the magnet of the testing equipment. As shown, Magnetic Bead 406 is functionalized with streptavidin 408 and, for the purposes of testing using the model bead construct, HRP 410 is bound to the streptavidin 408. As provided below, the model bead construct 400 is contacted with an electrode detection surface 404 (biosensor chip 201 of FIG. 2) via association with magnet 402 and tested using the electrochemical cell 100 (FIG. 1).

The methodology for electrochemical detection testing of the model bead construct was as follows:

(12) Clean biosensor chip (including electrode detection surface 404) by sonicating chip in water, followed by acetone, followed by water and allow to dry;
(13) Assemble electrochemical testing cell by adding cleaned biosensor chip;
(14) Add the appropriate volume of model bead construct (based on calibration) from step 11 above to Eppendorf tube;
(15) Bring solution volume to 200.00 μL with Buffer;
(16) Separate model bead construct with magnet for 5 min and remove supernatant;
(17) Add 200.00 μL of TMB Solution (reporter molecule);
(18) Vortex for approximately 5 seconds;
(19) Inject 150.00 μL into the fluid inlet of the electrochemical testing cell with the magnet down;
(20) Begin measurement;
(21) Signal magnet via microcontroller;
(22) Wait 5 seconds for measurement to start;
(23) Wait 25 seconds for magnet to rise; and
(24) Collect measurement for 200 seconds.

Figure 5:
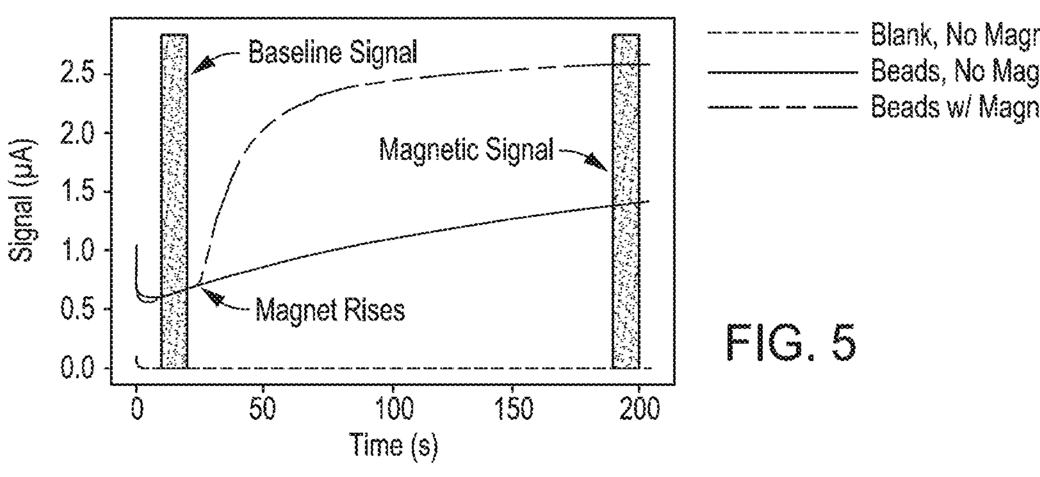
FIG. 5 is a plot of electrochemical signal response of the model bead construct, according to one or more aspects of the present disclosure.

Model Construct Test Example 1: In this testing Example, the electrochemical signal using the electrochemical testing cell was evaluated comparing (1) no model bead construct and magnet down (i.e., no magnetic field); (2) model bead construct and magnet down; and (3) model bead construct and magnet risen. The results are shown in FIG. 5. As shown, the blank exhibits no electrochemical signal, the model bead construct even in the absence of the magnet shows comparatively elevated electrochemical signal, and the model bead construct in the presence of the magnet shows a significantly even greater electrochemical signal. The magnetic enrichment of the model bead construct in the presence of the magnet begins when the magnet is raised to the back of the chip, approximately 25 seconds after the start of the measurement (see FIG. 1).

Figure 6A:
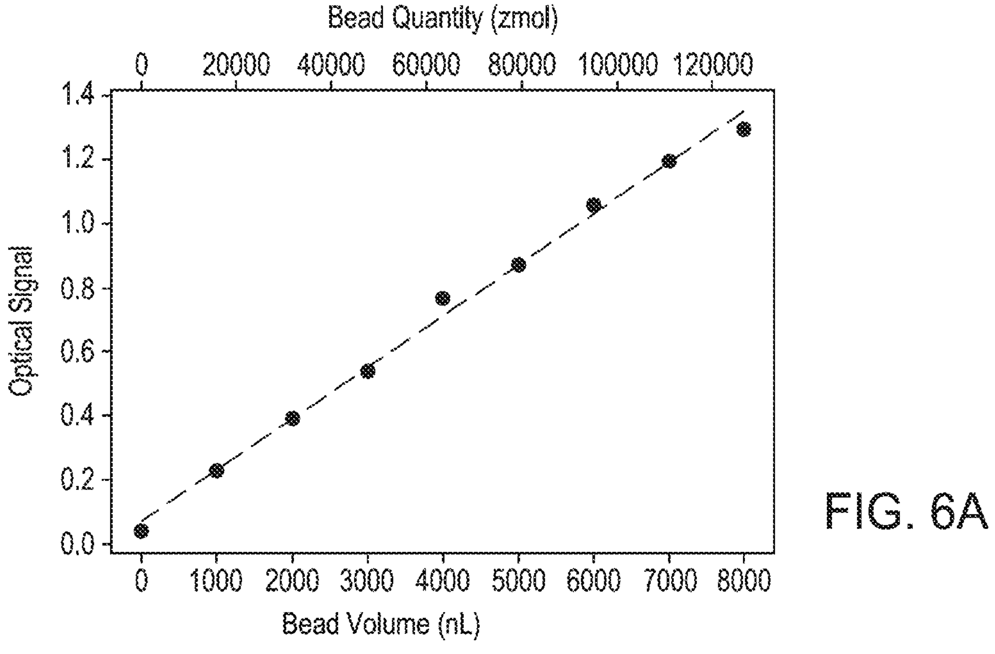
FIG. 6A is a plot of optical measurement calibration of the model bead construct, according to one or more aspects of the present disclosure.
Figure 6B:
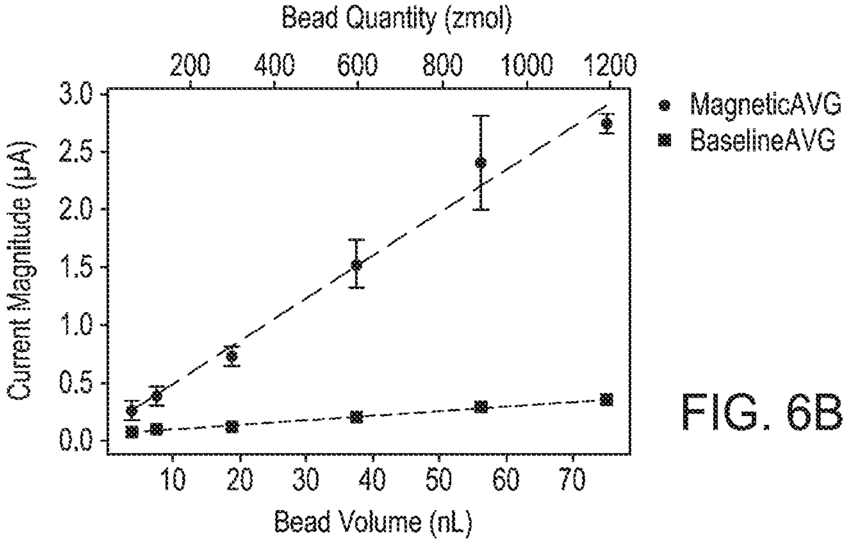
FIG. 6B is a plot of electrochemical measurement calibration of the model bead construct, according to one or more aspects of the present disclosure.

Model Construct Test Example 2: In this testing Example, calibration results for the various amounts of model bead construct at various quantities (provided in terms of the volume of beads from the stock solutions that were added in nanoliters (nL) or the quantity of the beads in zeptomoles (zmol) were evaluated using both optical measurements (arbitrary units) using traditional ELISA to compare with and electrochemical measurements (microamperes (μA)). FIG. 6A represents the optical measurement calibration and FIG. 6B represents the electrochemical measurement calibration (using a single gold macroelectrode detection surface) with magnetic enrichment (in the presence of magnet) and without magnetic enrichment (in the absence of magnet). As shown, the optical and electromagnetic signals demonstrate generally linear response as model bead construct concentration increases.

Figures 7A, 7B, 8:
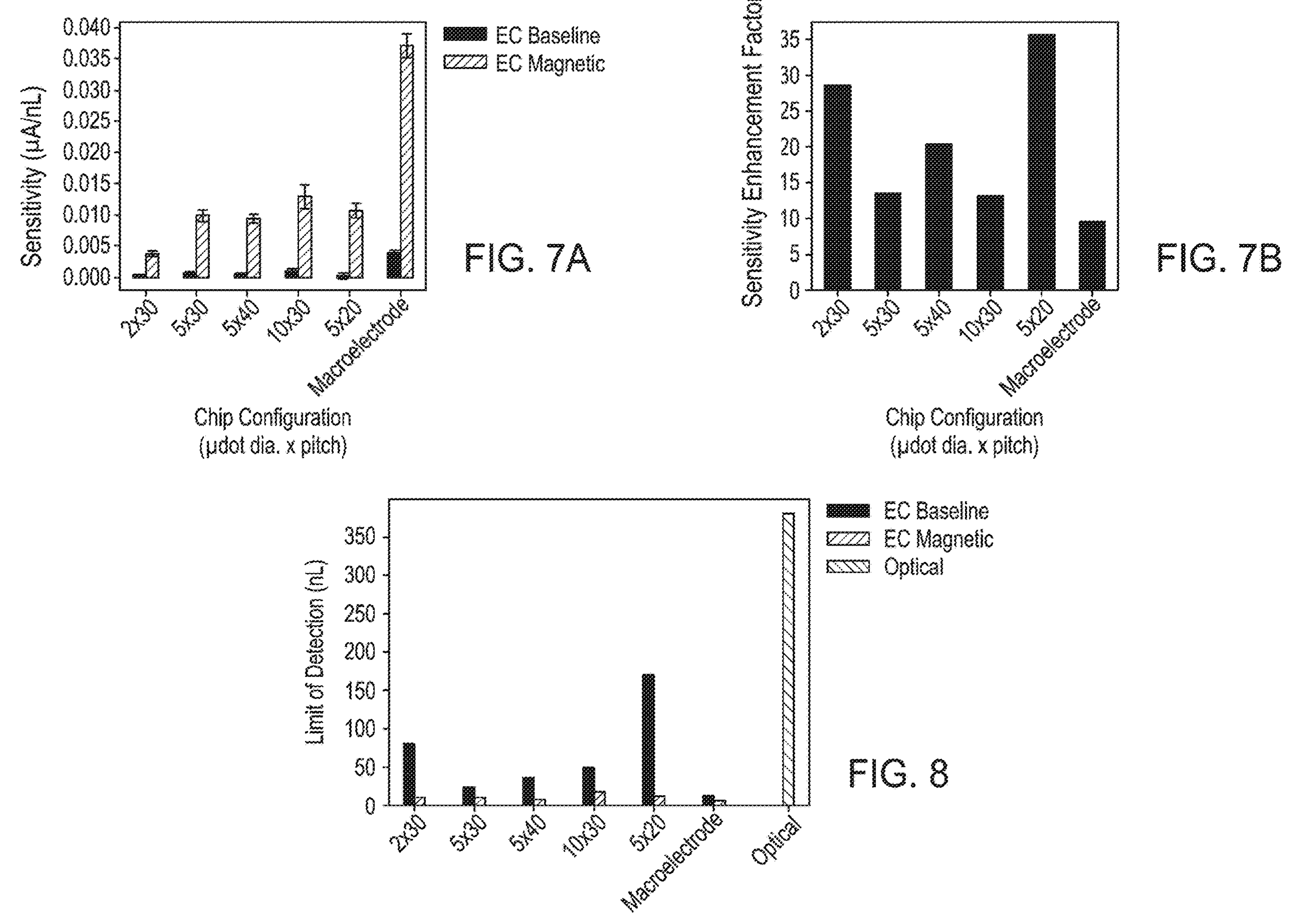
FIG. 7A is a plot of electrochemical signal sensitivity as a factor of microelectrode array configuration, according to one or more aspects of the present disclosure.
FIG. 7B is a plot of sensitivity enhancement factors of the results of FIG. 7A.
FIG. 8 is a plot of optical limits of detection as a factor of microelectrode array configuration, according to one or more aspects of the present disclosure.

Model Construct Example 3: In this Example, the electrochemical signal sensitivity for the model bead construct was evaluated and optimized using various microelectrode array configurations of microdot diameter and microdot interspatial distance. FIG. 7A shows a plot of sensitivity (μA per nL) for various array configurations provided along the x-axis and represented as microdot diameter×interspatial distance in μm (i.e., 2×30 is 2 μm diameter microdots×30 μm interspatial distance), compared to a single unpatterned macroelectrode detection surface. Each configuration tested with ("Magnet") and without ("Baseline") magnetic enrichment. As shown, the larger the diameter of the electrode detection surface, the greater the sensitivity. FIG. 7B shows the sensitivity enhancement factor represented by magnetic sensitivity divided by baseline sensitivity.

Model Construct Example 4: In this Example, the limits of detection (LOD) were evaluated based on microelectrode array configurations with respect to FIGS. 6B and 7A. The results are shown in FIG. 8. The term "optical" in FIG. 8 refers to measurements obtained with the model bead construct and optical detection using a UV-Vis plate reader used in traditional ELISA rather than electrochemical detection. The LOD refers to the volume of the model bead construct solution added and is strictly for comparison to optical measurements and is calculated from the statistics of linear regression of calibration data provided herein by the equation: LOD=(3*(standard deviation of intercept/slope)).

Statistical results for the Model Construct Examples are shown in Tables 1 and 2 below. Table 1 shows the electrochemical measurements and LOD measurements represented in FIGS. 7A, 7B, and 8. Table 2 shows the electrochemical sensitivity measurement and LOD measurement represented by FIGS. 6A and 8. Note, with reference to Table 2, that sensitivity of the optical measurement is not necessarily comparable to electrochemical measurement due to fundamental differences in methods and instrumentation used. Further, it is to be appreciated that LOD is better (i.e., lower in value) using electrochemical detection compared to optical detection.

TABLE 1

| | Baseline | | Magnetic | | Sensitivity Enhancement |
|---|---|---|---|---|---|
| Chip Size | Sensitivity (uA/nL) | LOD (nL) | Sensitivity (uA/nL) | LOD (nL) | Magnetic Factor |
| 5 × 20 | 2.99E−04 | 170.2 | 1.07E−02 | 13.44 | 35.7 |
| 5 × 30 | 7.24E−04 | 24.34 | 9.85E−03 | 11.91 | 13.6 |
| 5 × 40 | 4.61E−04 | 36.38 | 9.37E−03 | 8.299 | 20.3 |
| 10 × 30 | 9.86E−04 | 49.34 | 1.30E−02 | 19.15 | 13.1 |
| 2 × 30 | 1.33E−4 | 80.89 | 3.81E−3 | 10.46 | 28.6 |
| Macroelectrode | 3.90E−03 | 12.87 | 3.71E−02 | 6.281 | 9.5 |

TABLE 2

| Model Construct | Sensitivity (units/nL) | LOD (nL) |
|---|---|---|
| Optical Method | 1.60E−04 | 380.2 |

Full Bead Construct Examples

The full bead construct was developed (magnetic beads and detection beads functionalized with HRP to screen electrochemical methodologies and different microelectrode array configurations and to assess electrochemical and compared to optical performance and magnetic enhancement for detecting a biological molecule of SARS-COV-2 antigen.

The full bead construct was prepared by separately preparing various components: biotinylation of antibodies, the magnetic immobilization construct, and the detection construct. Each is described below. Biotinylization of antibodies was prepared as follows:

(1) Add 2.00 mg of EZ-LINK™ Biotin (ThermoFisher Scientific) to 590 μL of dimethyl sulfoxide (DMSO) immediately before use ("Biotin Solution");

(2) Add 1.33 μL of Biotin Solution to 100.0 μL of SARS-COV-2 N-Protein immobilization antibody in phosphate buffered saline (PBS);

(3) Add 0.66 μL of Biotin Solution to 100.0 μL of SARS-COV-2 N-Protein detection antibody in PBS;

(4) Incubate at RT for 30 min;

(5) Prepare 10 kilodaltons (kDa) molecular weight cut off Slide-A-Lyzer™ MINI Dialysis Device (ThermoFisher Scientific) (0.5 mL) according to manufacturer protocol using PBS (1×);

(6) Dialyze against PBS (1×) at RT using magnetic bar agitation for 2 hours;

(7) Replace PBS;

(8) Repeat steps 6 and 7 once;

(9) Dialyze overnight;

(10) Recover protein and perform quantification using UV-Vis.

The immobilization microbead construct was prepared as follows:

(11) Add 50.0 μL (0.5 mg) of Magnetic Beads into a microcentrifuge tube;

(12) Place the tube into a magnetic stand for 3 min to collect the beads against the side of the tube;

(13) Remove and discard the supernatant;

(14) Add 1.00 mL Buffer to the tube;

(15) Vortex gently and collect the beads with a magnetic stand;

(16) Remove and discard the supernatant;

(17) Suspend the Magnetic Beads in 300.0 μL Buffer;

(18) Add 15.00 μg of biotinylated immobilization antibody prepared in step 10 to the tube;

(19) Incubate for 1 hour and 40 min (700 rpm constant agitation) at RT;

(20) Repeat steps 12 to 14 ten times;

The detection microbead construct was prepared as follows:

(21) Add 277.0 μL of Buffer into a microcentrifuge tube;

(22) Add 3.00 μL of biotinylated HRP (2.5 mg/mL) to the tube;

(23) Add 2.80 μg of biotinylated N-Protein detection antibody prepared in Step 10 to the tube;

(24) Add 10.0 μL (0.108 mg) of POWER-BIND™ Streptavidin Coated Microparticles (ThermoFisher Scientific) (10.8 mg/mL) to the tube;

(25) Homogenize by pipetting up and down;

(26) Incubate for 1 hour and 40 min (700 rpm constant agitation) at RT;

(27) Centrifuge at 14000 centrifugal force (×g) at 4° C. for 30 min;

(28) Remove and discard supernatant;

(29) Suspend pellet in 1.00 mL of Buffer; and

(30) Repeat steps 27 to 29 nine times.

Microbead loading for the magnetic immobilization construct and detection construct in number of molecules per particle are provided in Table 3:

TABLE 3

| | Magnetic Immobilization Construct | Detection Construct |
|---|---|---|
| Antibody | 126,127 | 1,205 |
| HRP Enzyme | N/A | 4,857 |

Figure 9A:
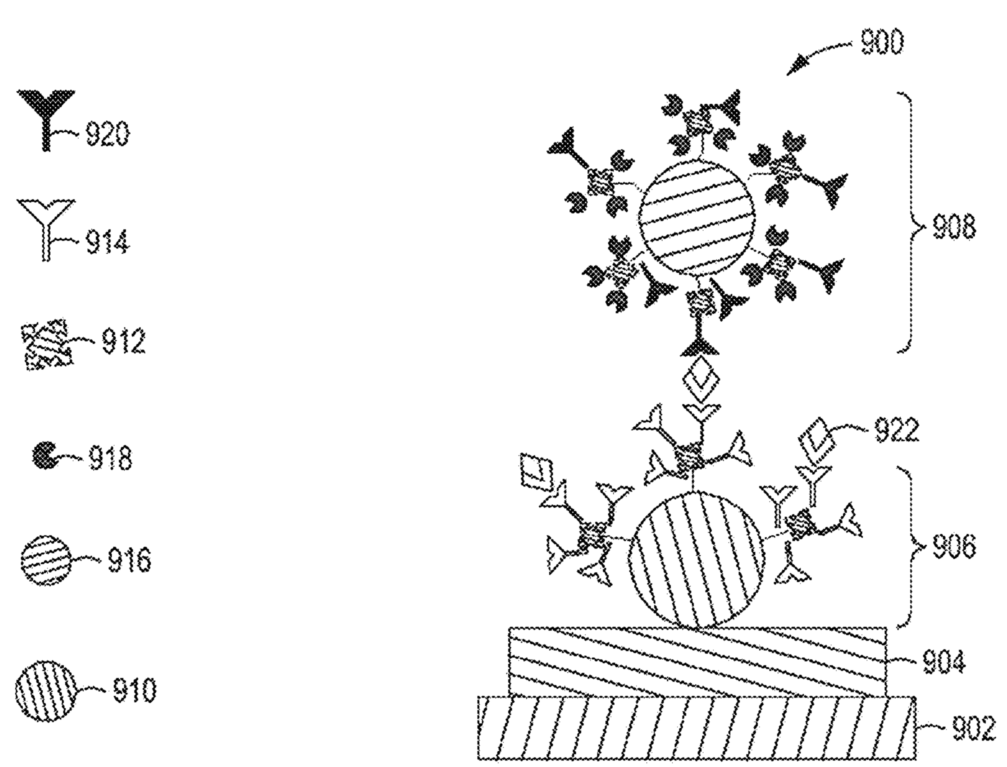
FIG. 9A illustrates a schematic of the full bead construct in association with the magnet of the electrochemical testing cell, according to one or more aspects of the present disclosure.

FIG. 9A illustrates a schematic of the full bead construct 900 in association with the magnet 902 of the testing equipment. As shown, full bead construct 900 comprises magnetic immobilization construct 906 and detection construct 908. The magnetic immobilization construct 906 comprises Magnetic Bead 910 co-functionalized with streptavidin 912 and SARS-COV-2 N-Protein immobilization antibodies 914. The detection construct 908 comprises polystyrene microbead 916 functionalized with streptavidin 912 and co-functionalized with HRP 918, and SARS-COV-2 N-Protein immobilization antibodies 920. The immobilization antibodies 914 and detection antibodies bind to a biological molecule of interest 922, such as SARS-COV-2 N-Protein in this configuration, and thus cause the interaction between the immobilization construct 906 and the detection construct 908. The immobilization construct 906 is contacted with the electrode detection surface 904 via magnetic association with the magnet 902. The full bead construct 900 is tested using the electrochemical cell 100 (FIG. 1), as described above with reference to the model bead construct.

Figure 9B:
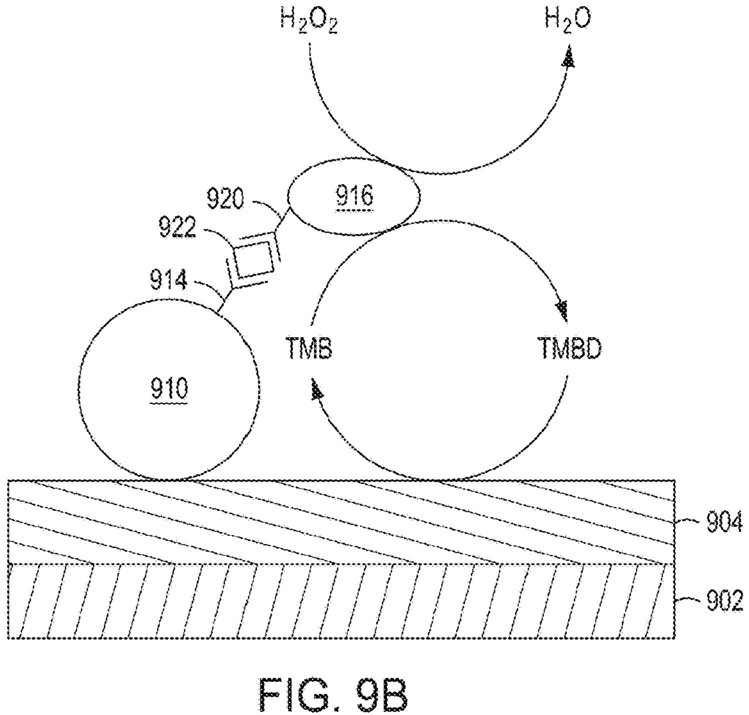
FIG. 9B illustrates a schematic reaction cascade for the full bead construct of FIG. 9A.

FIG. 9B illustrates a reaction cascade based on a simplified visualization of the full bead concept 900 of FIG. 9A. Like reference numbers are used for like structures between FIG. 9A and FIG. 9B. It is noted that while certain elements of FIG. 9A are not present in FIG. 9B, they are presumed to be present; FIG. 9B is simplified to emphasize the reaction cascade.

An HRP reaction is shown in FIG. 9B, in which a microbead 916 functionalized with streptavidin 912 which is co-functionalized with HRP enzyme 918 and SARS-COV-2 N-Protein detection antibodies 920 to form the detection construct 908 that reacts with an electrochemical reporter molecule TMB that is added to the fluid for detection of biological molecules 922 (SARS-COV-2 N-Protein) using the electrochemical testing cell 100 of the present disclosure. Additional elements include the Magnetic Bead 910 co-functionalized with streptavidin 912 and SARS-COV-2 N-Protein immobilization antibodies 914, electrode detection surface 904, and magnet 902. As shown, the HRP undergoes a catalytic, enzymatic reaction whereby an electrochemical reporter molecule, shown as TMB, and hydrogen peroxide (H2O2) react to produce TMBD (diimine analog of TMB) and water (H2O). The resulting TMBD product then reacts at the electrode detection surface 904 resulting in the regeneration of TMB. Because the enzymatic reporter (HRP) 918 is in close proximity to the electrode detection surface 904, the regenerated TMB is free to repeat the enzymatic reaction indefinitely. This prevents localized depletion of TMB and creates a positive feedback loop, resulting in improved signal.

The methodology for electrochemical detection testing of the full bead construct was as follows:

(1) Add 150.0 μL of Deactivation Solution (Lysis buffer for SARS-CoV-2 Antigen Test Development (Acro Biosystems, Newark, Delaware)) to 3 mL of Viral Transport Media (VTM) (Innovative Research, Nove, Michigan);

(2) Add 3.00 μL (1.5 μg) of magnetic immobilization construct (0.5 mg/mL) prepared as described above to 96.0 μL VTM in a 96 well plate;

(3) Add 1.00 μL of recombinant SARS-COV-2 N-Protein (0.3 mg/mL), for negative control, add 1.00 μL of Buffer in separate wells;

(4) Incubate for 1 hour 40 minutes at (450 rpm continuous agitation) at RT;

(5) Apply magnet for 3 min;

(6) Remove supernatant;

(7) Remove magnet;

(8) Add 200.0 μL of Buffer;

(9) Resuspend the pellet by pipetting up and down;

(10) Repeat steps 5 to 8 two times;

(11) Repeat step 5 to 7 once;

(12) Add 85.0 μL of Buffer;

(13) Add 15.0 μL of detection construct (0.162 μg) prepared as described above and homogenize by pipetting up and down;

(14) Incubate for 1 hour (450 rpm continuous agitation) at RT;

(15) Repeat steps 5 to 8 six times and leave reaction in the last step of the washing step while completing steps 16 to 17;

(16) Clean biosensor chip (including electrode detection surface) by sonicating chip in water, followed by acetone, followed by water and allow to dry;

(17) Assemble electrochemical testing cell by adding cleaned biosensor chip;

(18) Add full bead construct volume from step 15 above to Eppendorf tube;

(19) Bring solution volume to 200.0 μL with Buffer;

(20) Separate full bead construct with magnet (5 min) and remove supernatant;

(21) Add 200.0 μL TMB Solution (reporter molecule);

(22) Vortex for approximately 5 seconds;

(23) Inject 150.0 μL into the fluid cavity 116 of the electrochemical testing cell 100 with the magnet down;

(24) Begin measurement

(25) Signal magnet via potentiostat and microcontroller;

(26) Wait 5 seconds for measurement to start;

(27) Wait 25 seconds for magnet to rise; and

(28) Collect measurement for 200 seconds.

Figure 10:
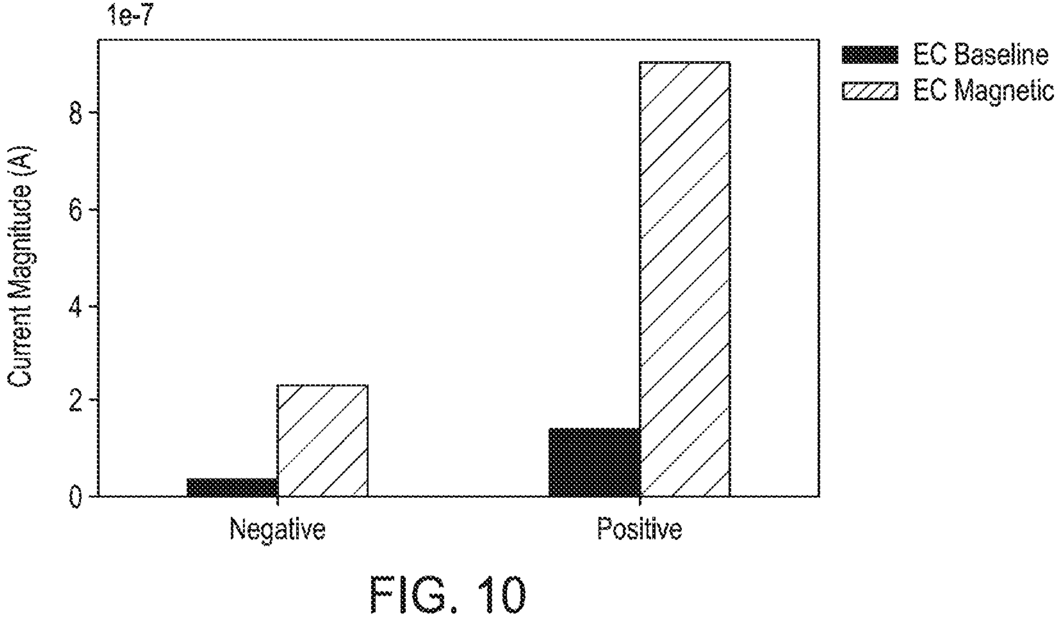
FIG. 10 is a plot of electrochemical signal response of the full bead construct, according to one or more aspects of the present disclosure.

Full Construct Example 1: In this Example, the electrochemical signal using the electrochemical testing cell was evaluated comparing (1) no full bead construct with magnet down (i.e., no magnetic field) and magnet raised; and (2) full bead construct with magnet down and magnet raised. The results are shown in FIG. 10. As shown, the blank ("Negative") exhibits very little comparative electrochemical signal, though a higher signal with the magnet raised; the full bead construct ("Positive") even in the absence of the magnet shows comparatively elevated electrochemical signal, and the full bead construct in the presence of the magnet shows a significantly even greater electrochemical signal. The results are further provided in Table 4 below.

TABLE 4

| | Baseline Signal (A) | Magnetically Enhanced Signal (A) |
|---|---|---|
| Negative | 3.54E−08 | 2.33E−07 |
| Positive | 1.38E−07 | 9.07E−07 |

Figure 11:
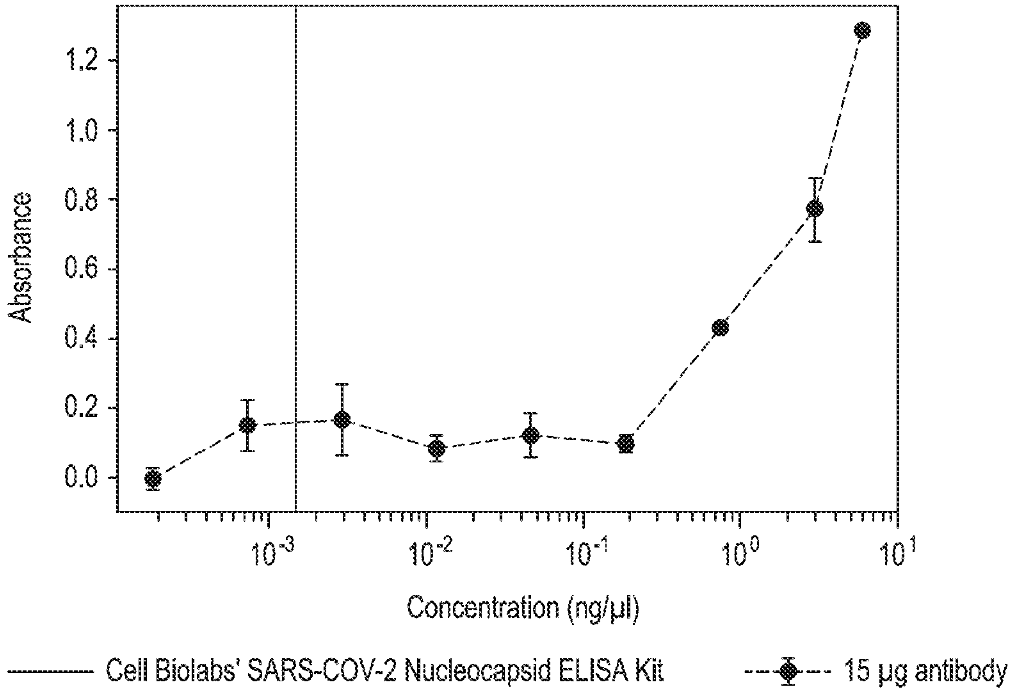
FIG. 11 is a plot of optical absorbance of the full bead construct based on Sars-COV-2 N-Protein concentration, according to one or more aspects of the present disclosure.

Full Construct Example 2: In this Example, optical absorbance measurements were evaluated based on increasing concentration of the SARS-CoV-2 N-Protein tested with full bead construct, and compared to commercially available SARS-COV-2 N-Protein ELISA kit (Cell Biolabs, Inc., San Diego, California) using UV-Vis. The results are shown in FIG. 11. The LOD value of the commercial kit appears as the vertical line. As shown, the full construct of the present disclosure exhibits greater absorbance at lower concentrations after background subtraction than the commercial ELISA kit, demonstrating LOD improvements, calculated to be 0.7 ng/mL of SARS-COV-2 N-Protein.

Accordingly, detection measurements from the Electrochemical ELISA-based biosensors of the present disclosure provide enhanced signal sensitivity compared to traditional ELISA plate-based approaches, as shown using both electrochemical and optical testing methodologies. When a sample is introduced to an electrochemical ELISA-based biosensor of the present disclosure, a biological molecule of interest (e.g., a viral antigen) is captured by the magnetic immobilization construct probe molecule(s) and detection construct probe molecule(s) (i.e., causing association between the immobilization construct and the detection construct). A magnet is introduced under the microelectrode array (and biosensor chip substrate) to draw the constructs to the electrode detection surface (e.g., of an electrode microarray). An electrochemical mediator may be added to react with the enzyme on the detection construct and generate an electrochemical signal. This electrochemical signal corresponds to the quantity of biological molecules of interest captured by the magnetic immobilization and detection constructs.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An electrochemical biosensor based on enzyme-linked immunosorbent assay, comprising:

an electrode detection surface;

a microbead detection construct comprising a plurality of signaling molecules; and a magnetic immobilization construct, wherein the magnetic immobilization construct comprises a magnetic microbead functionalized with a plurality of immobilization antibodies.

2. The electrochemical biosensor based on enzyme-linked immunosorbent assay of claim 1, wherein the electrode detection surface is a microelectrode array detection surface comprising a plurality of microdots.

3. The electrochemical biosensor based on enzyme-linked immunosorbent assay of claim 2, wherein the plurality of microdots have an average diameter in the range of about 1 μm to about 10 μm.

4. The electrochemical biosensor based on enzyme-linked immunosorbent assay of claim 2, wherein the plurality of microdots have an interspatial distance in the range of about 10 μm to about 50 μm.

5. The electrochemical biosensor based on enzyme-linked immunosorbent assay of claim 1, wherein the microbead detection construct comprises a detection microbead co-functionalized with a plurality of SARS-COV-2 N-Protein detection antibody and the plurality of signaling molecules.

6. The electrochemical biosensor based on enzyme-linked immunosorbent assay of claim 5, wherein the detection microbead is composed of a material selected from the group consisting of polystyrene, polycarbonate, ceramic, polypropylene, polyvinyl carbonate, silica, epoxy, and any combination thereof.

7. The electrochemical biosensor based on enzyme-linked immunosorbent assay of claim 5, wherein the detection microbead has a diameter in the range of about 0.1 μm to about 1.5 μm.

8. The electrochemical biosensor based on enzyme-linked immunosorbent assay of claim 5, wherein the plurality of detection antibodies detect SARS-COV-2 N-Protein.

9. The electrochemical biosensor based on enzyme-linked immunosorbent assay of claim 1, wherein the plurality of signaling molecules are electrochemical signaling molecules.

10. The electrochemical biosensor based on enzyme-linked immunosorbent assay of claim 1, wherein the plurality of signaling molecules are horseradish peroxidase enzymes.

11. The electrochemical biosensor based on enzyme-linked immunosorbent assay of claim 1, wherein the magnetic microbead is composed of a ferro-magnetic material selected from the group consisting of but not limited to iron oxide, nickel, cobalt and any combination thereof.

12. The electrochemical biosensor based on enzyme-linked immunosorbent assay of claim 1, wherein the magnetic immobilization construct is contacted with the electrode detection surface by magnetic field interaction with a magnet located beneath the electrode detection surface.

13. The electrochemical biosensor based on enzyme-linked immunosorbent assay of claim 1, wherein the microbead detection construct and the magnetic immobilization construct are configured to bind a target biological molecule, and wherein the microbead detection construct and the magnetic immobilization construct associate upon both binding the target biological molecule of interest.

14. A method comprising:

providing an electrochemical biosensor based on enzyme-linked immunosorbent assay, the sensor comprising:
- an electrode detection surface;
- a microbead detection construct comprising a plurality of signaling molecules; and
- a magnetic immobilization construct, wherein the magnetic immobilization construct comprises a magnetic microbead functionalized with a plurality of immobilization antibodies;

exposing the sensor to a plurality of reporter molecules;

contacting the sensor with a magnet;

detecting the presence of one or more biological molecules based on one or both of an electrochemical signal or an optical signal from at least a portion of the plurality of reporter molecules.

15. The electrochemical biosensor based on enzyme-linked immunosorbent assay of claim 14, wherein the magnetic microbead has a diameter in the range of about 0.1 μm to about 1.5 μm.

16. The electrochemical biosensor based on enzyme-linked immunosorbent assay of claim 14, wherein the plurality of immobilization antibodies detects SARS-COV-2 N-Protein.

17. The method of claim 14, wherein the exposing is before the contacting or the contacting is before the exposing.

18. A system comprising:

an electrochemical biosensor based on enzyme-linked immunosorbent assay;

a frame having a top and a bottom;

a plunger comprising a solenoid and a magnet, wherein the magnet is located above the solenoid and toward the top of the frame, the plunger for vertically moving toward the top and toward the bottom of the frame; and a recess in top of the frame for receiving an electrochemical biosensor based on enzyme-linked immunosorbent assay, wherein vertically moving the plunger toward the top of the frame causes the magnet to interact with the electrochemical biosensor based on enzyme-linked immunosorbent assay when the electrochemical biosensor based on enzyme-linked immunosorbent assay is received by the recess, and wherein vertically moving the plunger toward the bottom of the frame prevents the magnet from interacting with the electrochemical biosensor based on enzyme-linked immunosorbent assay when the electrochemical biosensor based on enzyme-linked immunosorbent assay is received by the recess.

19. The system of claim 18, wherein the electrochemical biosensor based on enzyme-linked immunosorbent assay comprises:

an electrode detection surface;

a microbead detection construct comprising a plurality of signaling molecules; and a magnetic immobilization construct.

* * * * *